US012788557B2

(12) United States Patent
Tranquillo et al.

(10) Patent No.: US 12,788,557 B2
(45) Date of Patent: Nov. 10, 2026

(54) PROSTHETIC VALVES AND METHODS OF MAKING

(71) Applicant: Regents of the University of Minnesota, Minneapolis, MN (US)

(72) Inventors: Robert Tranquillo, Arden Hills, MN (US); Zeeshan Syedain, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 686 days.

(21) Appl. No.: 18/114,881

(22) Filed: Feb. 27, 2023

(65) Prior Publication Data

US 2024/0058119 A1 Feb. 22, 2024

Related U.S. Application Data

(63) Continuation of application No. 16/500,147, filed as application No. PCT/US2018/026502 on Apr. 6, 2018, now Pat. No. 11,589,982.

(60) Provisional application No. 62/482,500, filed on Apr. 6, 2017.

(51) Int. Cl.
*A61F 2/24* (2006.01)

(52) U.S. Cl.
CPC .... *A61F 2/2415* (2013.01); *A61F 2220/0058* (2013.01)

(58) Field of Classification Search
CPC .................. A61F 2/2415; A61F 2/2412; A61F 2220/0075; A61F 2240/002
See application file for complete search history.

(56) References Cited

U.S. PATENT DOCUMENTS

| | | | | |
|---|---|---|---|---|
| 5,713,950 | A | 2/1998 | Cox | |
| 6,666,886 | B1 | 12/2003 | Tranquillo et al. | |
| 8,192,981 | B2 | 6/2012 | Hoerstrup et al. | |
| 8,198,245 | B2 | 6/2012 | Niklason et al. | |
| 8,399,243 | B2 | 3/2013 | Bouten et al. | |
| 8,617,237 | B2 | 12/2013 | Hoerstrup et al. | |
| 8,636,793 | B2 | 1/2014 | Hoerstrup et al. | |
| 9,034,333 | B2 | 5/2015 | Brokopp et al. | |
| 9,126,199 | B2 | 9/2015 | Moritz et al. | |
| 9,127,242 | B2 | 9/2015 | Guertin et al. | |
| 9,556,414 | B2 | 1/2017 | Dahl et al. | |
| 9,650,603 | B2 | 5/2017 | Dahl et al. | |
| 9,657,265 | B2 | 5/2017 | Dahl et al. | |
| 9,737,400 | B2 * | 8/2017 | Fish | A61F 2/2418 |

(Continued)

FOREIGN PATENT DOCUMENTS

| | | |
|---|---|---|
| KR | 100880550 | 1/2009 |
| KR | 1020120004676 | 1/2012 |

(Continued)

OTHER PUBLICATIONS

Syedain et al., "Pediatric tri-tube valved conduits made from fibroblast-produced extracellular matrix evaluated over 52 weeks in growing lambs," Sci Transl Med, Mar. 2021, 13(585):eabb7225, 15 pages.

(Continued)

*Primary Examiner* — Suzette J Gherbi
(74) *Attorney, Agent, or Firm* — Fish & Richardson P.C.

(57) ABSTRACT

A novel prosthetic valve is described herein, as well as methods of making such novel prosthetic valves.

17 Claims, 12 Drawing Sheets

(56) References Cited

U.S. PATENT DOCUMENTS

| | | | | |
|---|---|---|---|---|
| 10,039,640 | B2 * | 8/2018 | Grundeman | A61F 2/2412 |
| 10,105,208 | B2 | 10/2018 | Tranquillo et al. | |
| 10,111,740 | B2 | 10/2018 | Tranquillo et al. | |
| 11,589,982 | B2 * | 2/2023 | Tranquillo | A61F 2/2412 |
| 2001/0011189 | A1 | 8/2001 | Drasler et al. | |
| 2005/0055079 | A1 | 3/2005 | Duran | |
| 2006/0246584 | A1 | 11/2006 | Covelli | |
| 2007/0061800 | A1 | 3/2007 | Cheng et al. | |
| 2007/0269789 | A1 | 11/2007 | Covelli et al. | |
| 2009/0319003 | A1 | 12/2009 | Castel et al. | |
| 2011/0020271 | A1 | 1/2011 | Niklason et al. | |
| 2012/0185038 | A1 * | 7/2012 | Fish | A61F 2/2418 493/405 |
| 2012/0230950 | A1 | 9/2012 | Niklason et al. | |
| 2013/0013083 | A1 * | 1/2013 | Blum | A61L 27/60 623/23.7 |
| 2014/0035805 | A1 | 2/2014 | Minnen et al. | |
| 2014/0058496 | A1 | 2/2014 | Tranquillo et al. | |
| 2014/0277416 | A1 * | 9/2014 | Matheny | A61P 9/06 623/2.15 |
| 2014/0330377 | A1 | 11/2014 | Niklason et al. | |
| 2015/0012083 | A1 * | 1/2015 | Dahl | A61F 2/06 623/23.71 |
| 2015/0088247 | A1 * | 3/2015 | L'Heureux | C12N 5/0656 435/375 |
| 2015/0164631 | A1 | 6/2015 | Tranquillo et al. | |
| 2015/0305860 | A1 | 10/2015 | Wang et al. | |
| 2016/0203262 | A1 | 7/2016 | Sheehy et al. | |
| 2017/0135805 | A1 | 5/2017 | Dahl et al. | |
| 2017/0296323 | A1 | 10/2017 | Engelmayr, Jr. et al. | |
| 2017/0306292 | A1 | 10/2017 | Dahl et al. | |
| 2018/0325650 | A1 | 11/2018 | Tranquillo et al. | |
| 2021/0100653 | A1 | 4/2021 | Tranquillo et al. | |

FOREIGN PATENT DOCUMENTS

| | | |
|---|---|---|
| KR | 1020150087386 | 7/2015 |
| WO | WO 2004/018008 | 3/2004 |
| WO | WO 2004/101012 | 11/2004 |
| WO | WO 2007/092902 | 8/2007 |
| WO | WO 2013/090878 | 6/2013 |
| WO | WO 2015/169869 | 11/2015 |
| WO | WO 2018/102826 | 6/2018 |
| WO | WO 2019/006430 | 1/2019 |
| WO | WO 2020/243298 | 12/2020 |

OTHER PUBLICATIONS

Cattermole et al., "The Normal Ranges of Cardiovascular Parameters Measured Using the Ultrasonic Cardiac Output Monitor," Physiol. Rep., Mar. 2017, 5(6):e13195, 9 pages.

Dahl et al., "Readily Available Tissue-Engineered Vascular Grafts," Sci. Transl. Med., Feb. 2011, 3(68):68ra9, 11 pages.

EP Extended Search Report in European Appln. No. 18780763.1, dated May 21, 2021, 9 pages.

PCT International Preliminary Report on Patentability in International Appln. No. PCT/US2018/026502, dated Oct. 17, 2019, 8 pages.

PCT International Search Report and Written Opinion in International Appln. No. PCT/US2018/026502, dated Jun. 19, 2018, 10 pages.

Reimer et al., "Implantation of a tissue-engineered tubular heart valve in growing lambs," Ann. Biomed. Eng., Feb. 2017, 45(2):439-51.

Reimer et al., "Pediatric Tubular Pulmonary Heart Valve From Decellularized Engineered Tissue Tubes," Biomaterials, Sep. 2015, 62:88-94.

Syedain et al., "A Completely Biological "Off-The-Shelf" Arteriovenous Graft That Recellularizes in Baboons," Sci. Transl. Med., Nov. 2017, 9(414):eaan4209, 11 pages.

Syedain et al., "Implantable arterial grafts from human fibroblasts and fibrin using a multi-graft pulsed flow-stretch bioreactor with noninvasive strength monitoring," Biomaterials, Jan. 2011, 32(3):714-22.

Syedain et al., "Implantation of Completely Biological Engineered Grafts Following Decellularization Into the Sheep Femoral Artery," Tissue Eng. Part A, Jun. 2014 20(11-12):1726-34.

Syedain et al., "Tissue engineering of acellular vascular grafts capable of somatic growth in young lambs," Nat. Commun., Sep. 2016, 7:12951, 12 pages.

Wu et al., "Fast-degrading elastomer enables rapid remodeling of a cell-free synthetic graft into a neoartery, " Nat. Med., Jul. 2012, 18(7):1148-53.

* cited by examiner

PROSTHETIC VALVES AND METHODS OF MAKING

CROSS-REFERENCE TO RELATED APPLICATIONS

This application is a Continuation and claims priority to U.S. application Ser. No. 16/500,147, filed on Oct. 2, 2019, which is a National Phase application under 35 U.S.C. § 371 of International Application No. PCT/US2018/026502, filed on Apr. 6, 2018, which claims priority to U.S. Application No. 62/482,500, filed on Apr. 6, 2017. The disclosure of the prior applications are considered part of the disclosure of this application, and are incorporated in their entirety into this application.

FEDERALLY SPONSORED RESEARCH OR DEVELOPMENT

This invention was made with government support under HL107572 awarded by the National Institutes of Health. The government has certain rights in the invention.

TECHNICAL FIELD

This disclosure generally relates to prosthetic valves and methods of making.

BACKGROUND

Unlike a wide variety of mechanical and bioprosthetic heart valves implanted and delivered via catheter into adult patients, a heart valve that can grow and maintain function for pediatric patients has not yet been demonstrated. The only accepted options for these children are valves made from chemically-fixed tissues that often become dysfunctional due to calcification and almost always will need to be replaced at least once since it has no growth capacity due to the chemical fixation. These children will need to endure at least one, usually several, and sometimes five open heart surgeries until adulthood, when a mechanical valve would typically be implanted, requiring lifelong anticoagulation therapy. Clearly, if a valve could be implanted the first time that is able to grow with the recipient (e.g., somatic growth; see, for example, Syedain et al., 2016, Nat. Commun., 7:12951. PMCID: 5052644), as well as development of a functional endothelium (see, for example, Syedain et al., 2016, Nat. Commun., 7:12951. PMCID: 5052644), it would alleviate immense suffering for these children and their families, and reduce an immense health care cost.

In addition, a major weakness of current prosthetic heart valves is the tendency of the commissures to fail, as the collapsing leaflet is constantly pulling against the connection with the outer supporting tube. This disclosure describes a multi-leaflet valve that is made by suturing tubular members together along their longitudinal axis as well as horizontally to define the leaflets, resulting in commissures that cannot fail in the manner current prosthetic valves fail and that are as strong as native material because they are formed by tubular members attached longitudinally, not within one another.

SUMMARY

This disclosure provides a novel prosthetic valve design, as well as methods of making such novel prosthetic valves. Engineered tissue, sometimes referred to as regenerative tissue, as used herein, refers to tissue formed from cells producing an extracellular matrix. Typically, prior to further processing, the tissue is decellularized. For example, some embodiments include combining matrix-producing cells, fibrinogen, and thrombin to produce a cell-seeded composition. The cell-seeded composition is then cultured in an appropriate cell culture medium, and then the extracellular matrix formed therefrom is decellularized.

In one aspect, a prosthetic valve is provided. Such a prosthetic valve typically includes a body comprising a first end, a second end, an outer surface, and annular region, and defining a longitudinal axis, the body including at least two tubular members aligned with the longitudinal axis; wherein each tubular member being fixedly attached to an adjacent tubular member along an adjoining exterior surface in a direction along the longitudinal axis such that portions of the exterior surface of the adjoined tubular members circumferentially form a wall of the body; wherein each tubular member being closed at the second end, the luminal surface of each tubular member defining the top surface of a leaflet, wherein the portions of the exterior surface at the first end of the adjoined tubular members that do not form the wall of the body define commissures.

In some embodiments, each leaflet includes a commissure region and an annulus region. In some embodiments, each leaflet is integral with the annular region of the body. In some embodiments, the commissure region and the annular region of each leaflet is contiguous (or integral with one another). In some embodiments, each leaflet and corresponding annular region of the body are formed by each tubular member.

In another aspect, a prosthetic valve is provided. Such a prosthetic valve typically includes a body comprising at least two adjoined tubular members closed at one end, wherein each closed tubular member forms a leaflet. As used herein, a valve can include one or more leaflets (e.g., two leaflets, three leaflets, four leaflets).

In still another aspect, a prosthetic valve is provided. Such a prosthetic valve typically includes a body defining a longitudinal axis; the body comprising at least two leaflets, each leaflet being defined by a tubular member aligned with the longitudinal axis, the tubular member including a first end, a second end, an exterior surface, and a luminal surface; the first end of the tubular member being open and the second end of the tubular member being closed such that the luminal surface of the tubular member forms a top surface of a leaflet.

The prosthetic valve described herein, including two tubular members. The prosthetic valve described herein, including three tubular members. In some embodiments, the valve is a bi-leaflet valve. In some embodiments, the valve is a tri-leaflet valve. Representative valves include, without limitation, mitral valves, aortic valves, tricuspid valves, pulmonary heart valves, and venous valves. In some aspects, use of the prosthetic valve described herein is provided for the treatment of valve insufficiency or failure.

In yet another aspect, a method of making a prosthetic valve is provided. Such a method typically includes providing at least two tubular members, each of the tubular members including a first end, a second end, an exterior surface, and a luminal surface and defining a longitudinal axis; aligning the at least two tubular members along the longitudinal axis; attaching adjacent tubular members along an adjoining exterior surface in a direction along the longitudinal axis to form a body, the body including a first end, a second end, an outer surface, and annular region, and defining a longitudinal axis, wherein portions of the exterior surface of the adjoined tubular members circumferentially form a wall of the body; and closing each tubular member at the second end such that the luminal surface of each tubular member defines the top surface of a leaflet, wherein the portions of the exterior surface at the first end of the adjoined tubular members that do not form the wall of the body define commissures.

In some embodiments, each of the tubular members are biologically-engineered tubular members, synthetic tubular members, native tissue, or a combination thereof. In some embodiments, the body comprises biologically-engineered tubular members, synthetic tubular members, or a combination thereof. In some embodiments, the attaching is with stitches, staples, adhesives (e.g. cyanoacrylate), or thermal fusion/welding. In some embodiments, the closing is with stitches, staples, adhesives (e.g. cyanoacrylate), or thermal fusion/welding.

A method as described herein can be performed with two tubular members. A method as described herein can be performed with three tubular members. In some embodiments, the valve is a bi-leaflet valve. In some embodiments, the valve is a tri-leaflet valve.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1A:
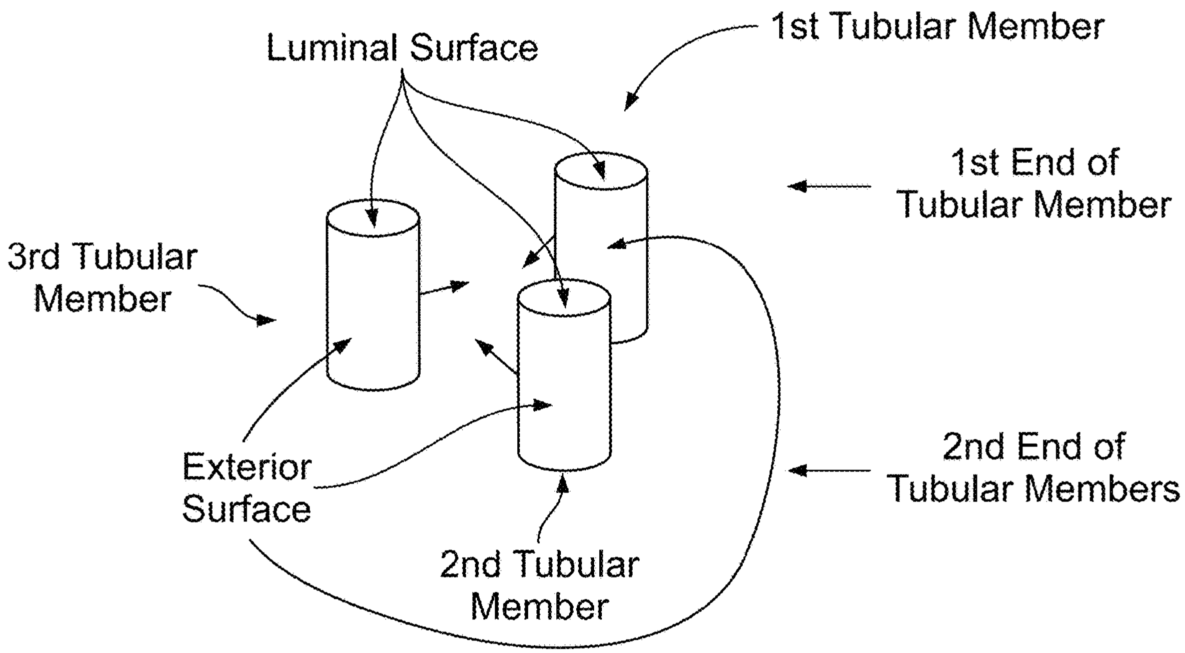
FIGS. 1A-1H are schematics showing a method of making a prosthetic valve as described herein.

Compositions and methods are described herein that allow for the production of a prosthetic valve. There is a dire need for a heart valve that can grow with children given that the current practice is to surgically implant and replace inert valves multiple times as the child outgrows them. Using a biologically-engineered collagenous matrix in the form of a tube that has been shown to grow as a pulmonary artery replacement in lambs (see, for example, Syedain et al., 2016, Nat. Commun., 7:12951. PMCID: 5052644), and a novel design for a heart valve made from sewing three of these tubes together with degradable suture that confers durable commissures as well as valve growth potential, this tri-tube design was tested in vitro and its function assessed in a preclinical model. The novel tri-tube design was shown to have superior commissure durability compared to a previous tube-in-tube design in accelerated fatigue testing, and it was shown to exhibit acceptable hydrodynamic performance in a pulse duplicator. Epicardial ultrasound performed at implantation in a juvenile sheep showed a non-regurgitant valve with <10 mm Hg pressure drop. The results described herein demonstrate the potential for durable commissures needed for long-term valve growth of this "off-the-shelf" tri-tube heart valve made from biologically-engineered tubes of collagenous matrix and degradable suture.

Representative valves that can be made using the compositions and methods described herein include, without limitation, mitral valves, aortic valves, tricuspid valves, pulmonary heart valves, and vein valves. The compositions and methods described herein provide for prosthetic valves that have a unique multi-tube design, which is different from a conventional prosthetic tubular heart valve based on a single collapsing tube that forms all the leaflets but suffers from weak commissures due to tube "pull-out". The prosthetic valves described herein can be used for the treatment of valve insufficiency or failure. As described herein, a prosthetic valve can include at least two adjoined tubular members that are closed (or fixedly closed, or sealed) at one end such that each closed member forms a leaflet.

As described in more detail below, completely biological tubes can be grown in vitro from human dermal fibroblasts entrapped in "sacrificial" fibrin gel tubes. Over a period of approximately 8 weeks, the fibroblasts convert the fibrin gel tube into a tube of circumferentially-aligned dense collagenous matrix, which is then detergent-decellularized to create an allograft that can be stored for at least 6 months without loss of mechanical properties.

Without intending to be limited to a particular process for producing engineered tissue, an exemplary method includes combining fibrinogen or the like, thrombin or the like, and extracellular matrix (ECM)-producing cells; and allowing the cells to grow sufficiently to produce ECM. One skilled in the art will recognize that up to nine passages (e.g., between five and nine passages, between seven and nine passages) typically optimizes ECM production. In some embodiments, the fibrinogen or the like, thrombin or the like, and extracellular matrix (ECM)-producing cells are combined in a suspension or gel and molded to the desired tubular shape.

The resulting engineered tissue may be characterized by its lack of crosslinking and its lack of generating an immune response. In some embodiments, the engineered tissue includes collagen or fibrous structures that are aligned. The engineered tissue of the present invention is distinct from certain other kinds of engineered tissue that does not involve an extracellular matrix in its production and/or includes cells in its final product.

This matrix exhibits a non-linear stress-strain curve typical of native tissue and possesses physiological compliance and a burst pressure that meets or exceeds that of native arteries. The resulting tensile mechanical properties compared well to ovine pulmonary valve leaflets in terms of modulus and ultimate tensile strength (UTS) measured in strain-to-failure testing. The same is also true for collagen content. It has been shown in preclinical studies in sheep for up to 12 months duration that these grafts, grown from ovine dermal fibroblasts, become populated by appropriate host cells (including endothelium formation) without a sustained inflammatory response, overt immune response, or calcification as arterial grafts and tubular heart valves and even grow as a pulmonary artery replacement with young lambs into adulthood. A similar positive remodeling without adverse outcomes has been shown in vascular grafts grown from human dermal fibroblasts and implanted into baboons as arterio-venous grafts for up to 6 months.

In a previous study (Reimer et al., 2017, Ann. Biomed. Eng., 45(2):439-51), a valve design was developed and tested based on these tubes and degradable suture, which, lacking any inert material, has somatic growth potential. One tube was placed inside a second tube, which were then sutured together at the base with three equi-spaced vertical suture lines, creating a tubular heart valve since the inner tube was constrained from collapsing inward at those three "commissure" points (FIG. 1A from Reimer et al., 2017, Ann. Biomed. Eng., 45(2):439-51). This valve has shown short term function in a growing lamb model, but the tube-in-tube design manifested a failure mode of commissure instability after 3-4 months implantation. This was evident in an explanted valve that was slit and laid flat (FIG. 4D of Reimer et al., 2017, Ann. Biomed. Eng., 45(2):439-51); while the tubes had fused together along much of the degradable suture line, essentially forming leaflets in situ, the initial locations of the commissures were several millimeters above the points of closest approach of the leaflets. This occurred in the absence of any leaflet thickening, suggesting the suture line defining the commissures at implantation was not stable to long-term exposure to cyclic diastolic (downward) force on the inner tube. It was speculated this caused a "sagging" of the inner tube through the vertical suture line over time and led to an effective decrease in leaflet height with attendant central valvular regurgitation before the possibility of valve growth (cells were present on most of the "leaflet" surfaces as early as 12 wk post-op but had not extensively recellularized the interior by 22 wk as would be needed for an increase in coaptation area to occur, in contrast to the "root" which was extensively recellularized by 12 wk (Reimer et al., 2017, Ann. Biomed. Eng., 45(2):439-51)). In order to eliminate this failure mode of unstable commissures in the original tube-in-tube design, a novel tri-tube valve design was conceived and is described herein.

Referring to FIG. 1, a structure that starts with three tubular members is shown, which ultimately results in a tri-leaflet prosthetic valve. However, it should be appreciated that the techniques described herein (and represented schematically in FIGS. 1A-1F) also can be applied to create a bi-leaflet prosthetic valve (i.e., starting with two tubular members; see, for example, FIGS. 1G and 1H) or a quad-leaflet prosthetic valve (i.e., starting with four tubular members). Thus, the tri-leaflet valve shown in FIGS. 1A-1F, as well as in FIGS. 2-6, 8A and 9A should be considered exemplary.

Specifically with respect to FIG. 1A, three tubular members are shown and correspond to the starting material. As shown in FIG. 1A, each tubular member includes a first end and a second end, and has an exterior surface and a luminal surface (i.e., the inside surface of each tubular member), which define a longitudinal axis. As shown in FIG. 1A, the tubular members are positioned parallel to one another (i.e., aligned along their longitudinal axes).

The tubular members that form the basis of the prosthetic valve described herein can be made from any material that is suitable for use in a prosthetic valve. Suitable materials include, for example, native tissue material (e.g., native vessels), biologically-engineered material (e.g., Syedain et al., 2011, Biomaterials, 32(3):714-22; or Dahl et al., 2011, *Sci. Transl. Med.,* 3(68):68ra9), synthetic material (e.g., Wu et al., 2012, *Nat. Med.,* 18(7):1148-53), or a combination thereof.

Some embodiments of the tubular members may include a degradable scaffold that can be seeded by extracellular matrix producing cells. The scaffold may be formed from fibrin, PLA, PGA, or other synthetic or biological polymer, and mixtures thereof. The ECM producing cells can be cultured with the scaffold, allowing the cells to produce ECM, which can in turn replace the degradable scaffold. Optionally, the scaffold can be manipulated or processed to create alignment of the fibers in the ECM (e.g., an anisotropic matrix). The final product may be decellularized using detergents, dehydrated (e.g., freeze drying), or fixed/cross-linked (e.g., glutaraldehyde fixation) to create engineered tissue with or without cells.

Some embodiments of the present invention may use the processes and engineered tissue as disclosed in the following, all of which are hereby incorporated by reference in their entirety: US 2007/061800; WO 2007/092902; US 2016/0203262; WO 2004/018008; WO 2004/101012; U.S. Pat. Nos. 8,192,981; 8,399,243; 8,617,237; 8,636,793; 9,034,333; 9,126,199; U.S. Ser. No. 10/523,618; U.S. Ser.

No. 10/556,959; U.S. Ser. No. 13/771,676; US 2015/0012083; US 2009/0319003; US 2011/0020271; US 2012/0230950; US 2013/0013083; US 2014/0330377; US 2015/0088247; US 2015/0305860; US 2014/035805; US 2017/0135805; US 2017/0296323; US 2017/0306292; U.S. Pat. Nos. 8,198,245; 9,127,242; 9,556,414; 9,657,265; and 9,650,603.

Since no structural element (e.g., metal or plastic frame) is required, either in the tubular members or to configure the leaflet, the prosthetic valves described herein are not structurally constrained and can allow for growth, if an appropriate material and degradable sutures are used. This feature is particularly significant for pediatric application of the prosthetic valves described herein. In addition, tubular members of various diameters can be used to produce a given target diameter for the valve, which also will lead to leaflets having different areas. This feature is particularly relevant as it pertains to valve performance under specified pressure-flow conditions.

In some embodiments, the individual tubular members within a prosthetic valve as described herein can be made from different materials. For example, in a bi-leaflet valve, one of the tubular members used in the starting materials can be a biologically engineered tubular member while the other tubular member used in the starting materials can be a synthetic tubular member. In another example, in a tri-leaflet valve, one of the starting tubular members can be a native tissue tubular member and the other two starting tubular members can be biologically-engineered tubular members. Virtually any combination of tubular members is envisioned.

Figure 1B:
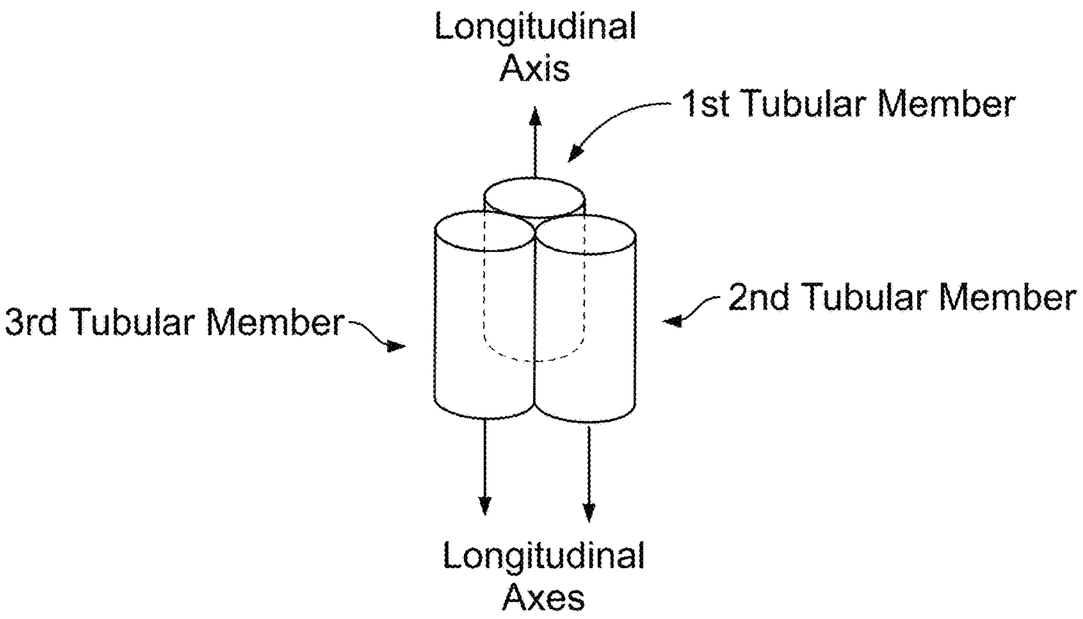
Figure 1C:
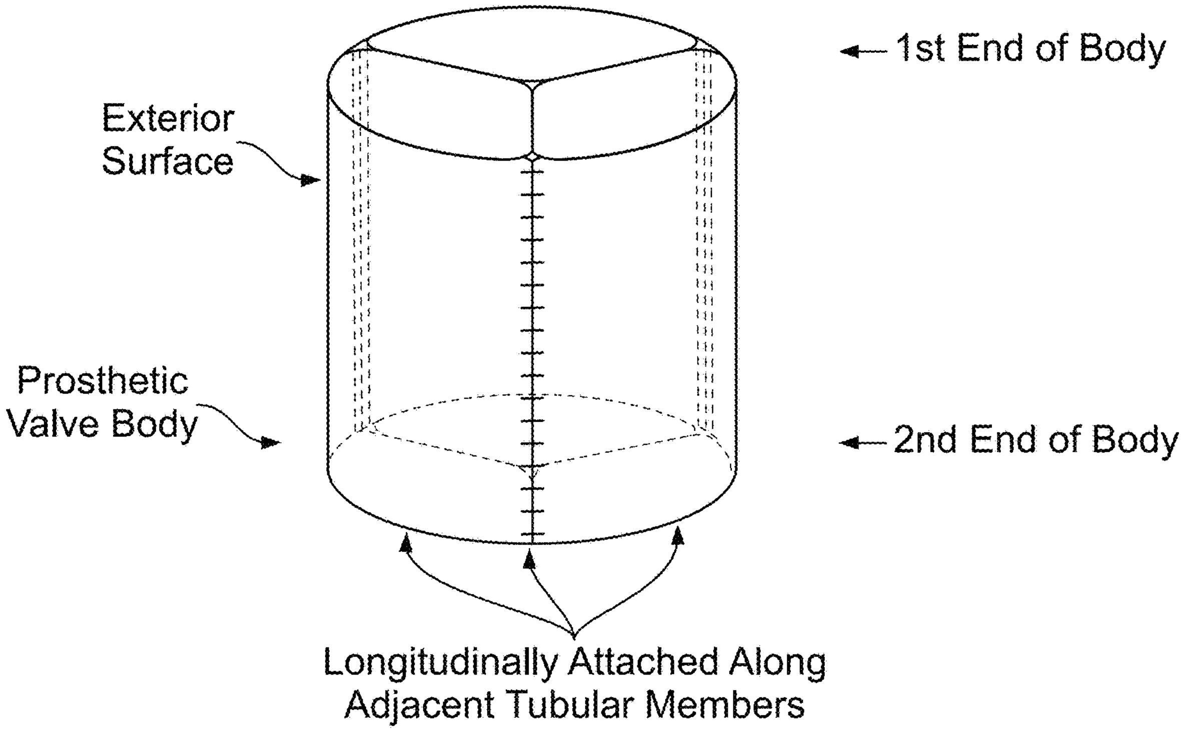
Figure 1D:
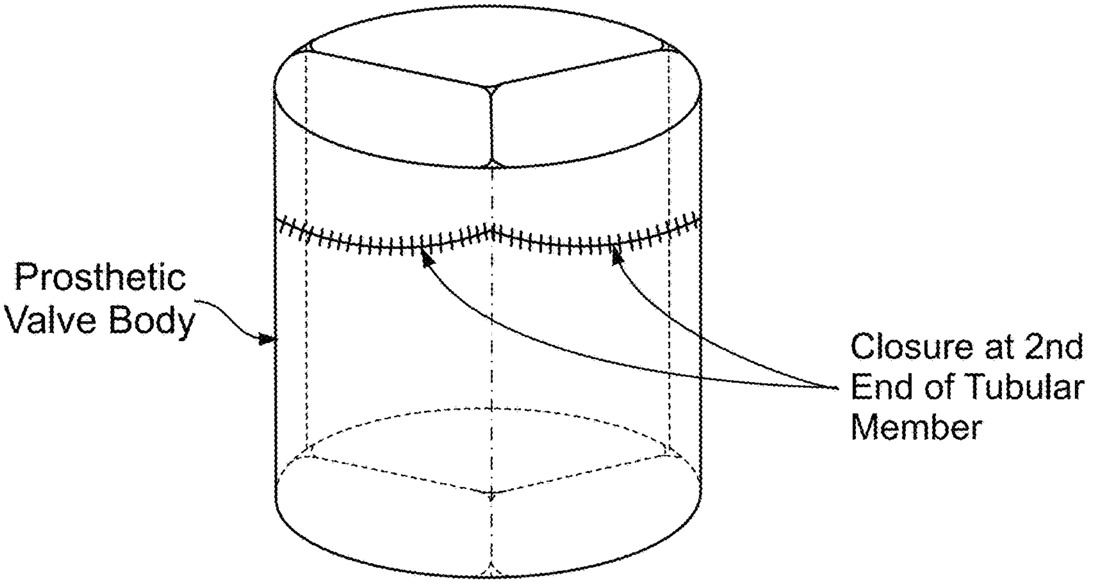

With respect to FIG. 1B, the aligned tubular members are brought into contact with one another and FIG. 1C shows that each of the tubular members are attached to the adjacent tubular member(s) along a longitudinal seam. The longitudinal seam is located between the adjoining exterior surfaces of each tubular member. As shown in FIG. 1C, portions of the exterior surface of the adjoined tubular members form a circumferential wall of a prosthetic valve body. Similar to each tubular member, the prosthetic valve body has a first end and a second end through which a longitudinal axis passes as well as an outer surface and an annulus.

Figure 2A:
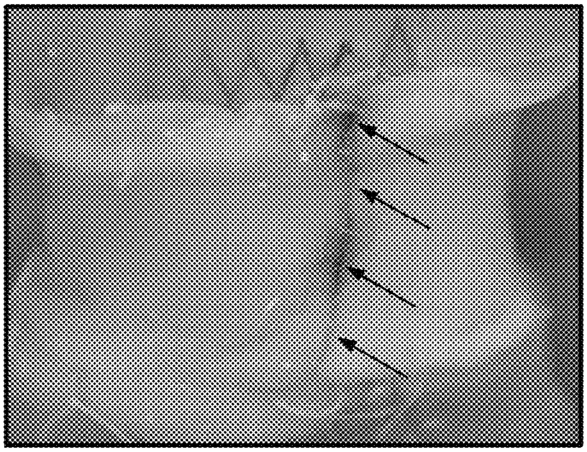
FIGS. 2A and 2B are photographs that each show a longitudinal seam (arrows) on the exterior surface of a prosthetic valve as described herein.
Figure 2B:
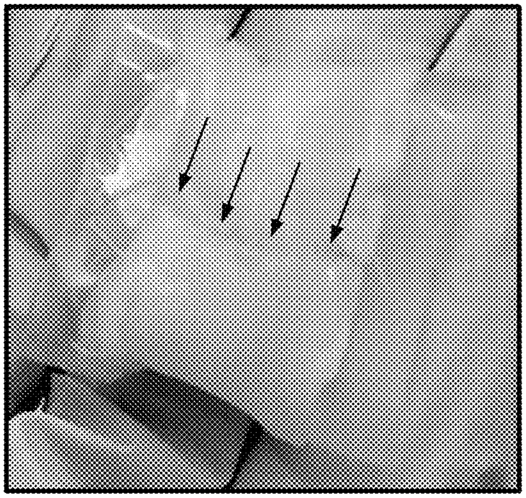

FIGS. 2A and 2B are photographs showing the exterior of a prosthetic valve body in which the longitudinal seam can be seen (arrows). In FIG. 2A, the longitudinal seam is shown vertically, while in FIG. 2B, the prosthetic valve body is shown horizontally, so the longitudinal seam is faintly detectable in the horizontal direction.

Figure 1E:
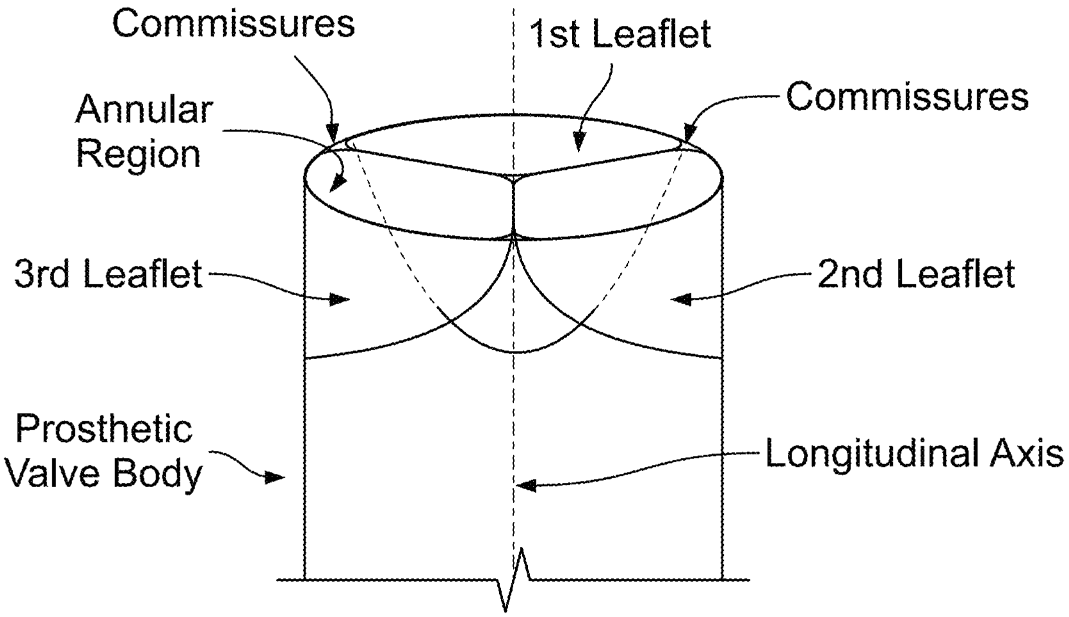
Figure 1F:
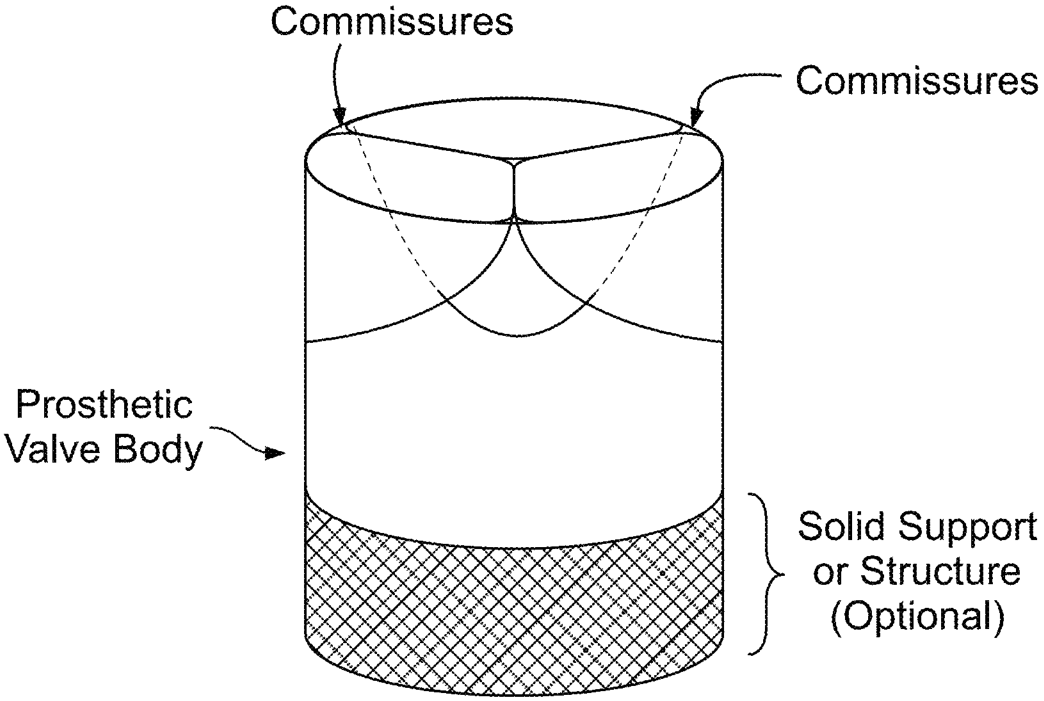

Returning now to FIG. 1, FIG. 1D shows that each tubular member is then closed at its second end. Closure at the second end of each tubular member creates a leaflet (or a cusp), with the top surface of each leaflet (i.e., the surface at the first end of the valve body) formed from the luminal (or inside) surface of each tubular member (FIG. 1E). The bottom surface of each leaflet (i.e., the surface that projects toward the second end of the valve body) is formed from a portion of the exterior surface of each adjoined tubular member that does not form part of the circumferential wall (FIG. 1E).

Figure 3:
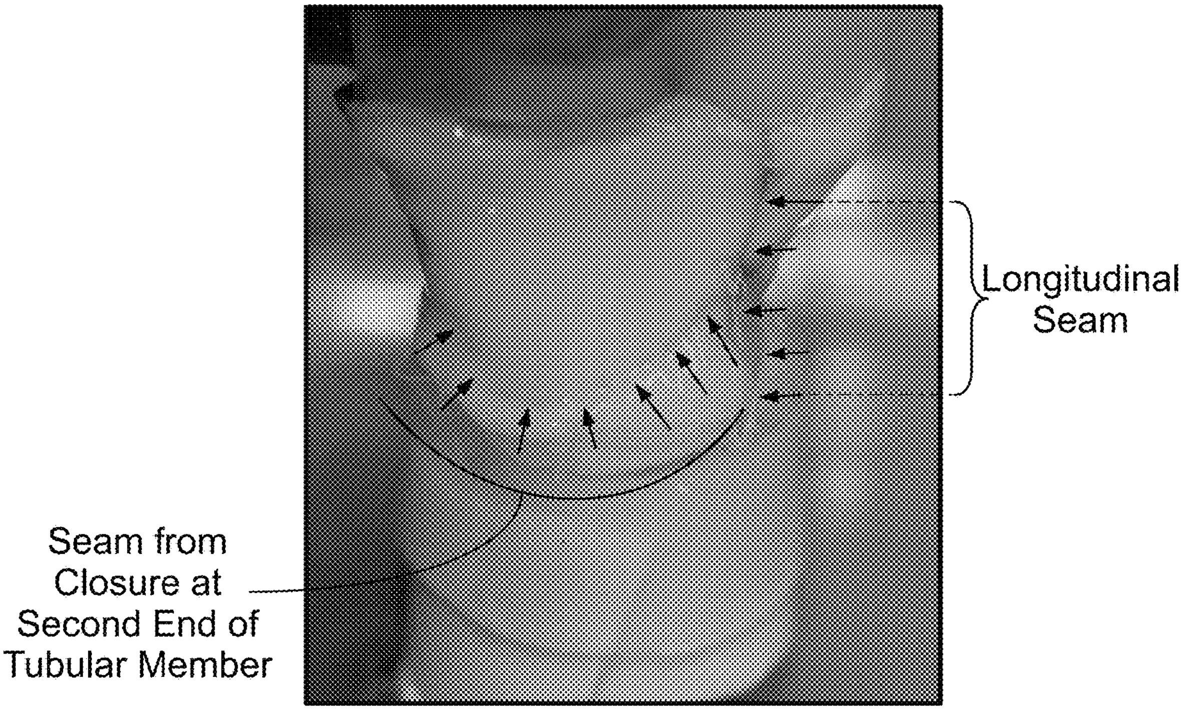
FIG. 3 is a photograph that shows a seam closing the second end of a tubular member (arrows) on the exterior surface of a prosthetic valve as described herein.

FIG. 3 is a photograph showing the exterior of a prosthetic valve body in which the longitudinal seam can be seen (blue line to the far right of the body; arrows) as well as the closure at the second end of the tubular member (arrows). In FIG. 3, the closure at the second end of the tubular member is shown as an upwardly curved closure (e.g., concave, relative to the first end of the prosthetic valve body), but the closure could be a straight horizontal closure or a downwardly curved closure or any combination thereof. The position and directionality of the closure will determine, at least in part, the shape and structural configuration that is desired for each leaflet.

Each leaflet has both a commissure region and an annular region. As shown in FIG. 1E, the portions of the exterior surface of the adjoined tubular members that do not form part of the circumferential wall of the body, at the first end, define the commissures of the valve, while the luminal surface of each tubular member that is opposite the exterior surface of each tubular member that forms the circumferential wall of the body, at the first end, defines the annular region of each leaflet. Due to the tubular structure by which each leaflet is generated, the commissure region and the annular region of each leaflet is contiguous (or integral with one another), and each leaflet, including the commissure and the annular region are formed by a single tubular member. As shown in FIG. 1E, each leaflet includes a commissure region that is seamlessly continuous with an annulus region.

Figure 4A:
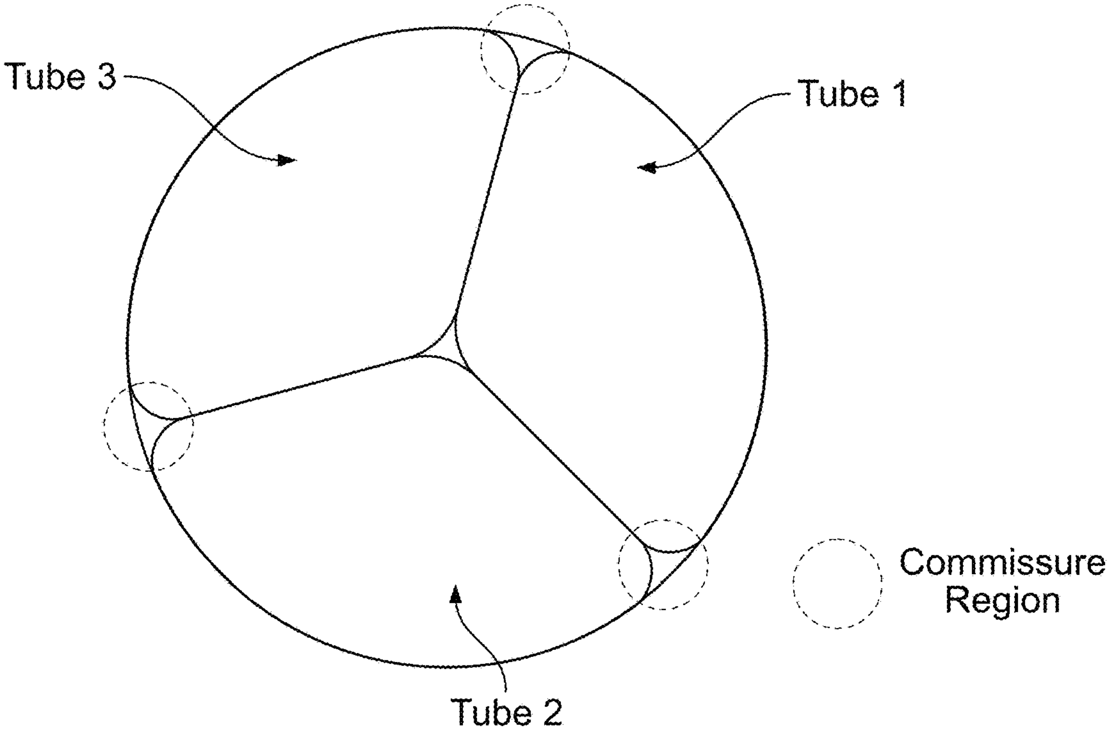
FIG. 4A is a schematic showing an end view (i.e., from the first end) of a prosthetic valve as described herein, showing the layout of three tubular members and how they form commissures.
Figure 4B:
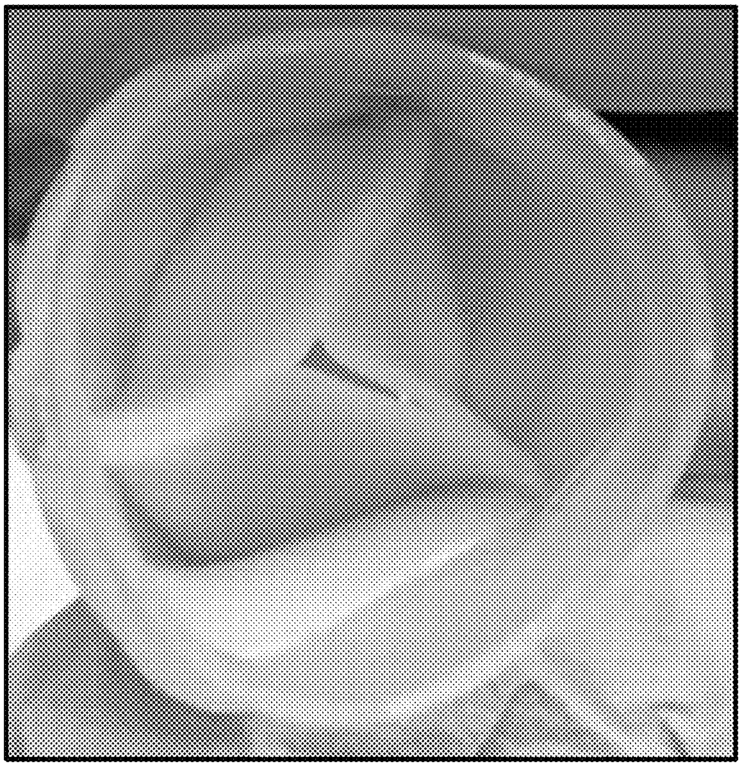
FIG. 4B is a photograph showing an end view (i.e., from the first end) of a prosthetic valve as described herein, showing the top surface of the leaflets and the commissures.

FIG. 4A is a schematic showing an end view (i.e., a view of the first-end) of a prosthetic valve as described herein and schematically demonstrating how the commissures are formed from the tubular members and the position of the longitudinal attachments. FIG. 4B is a photograph showing an end view (i.e., a view of the first-end) of a prosthetic valve as described herein and demonstrating the formation of the leaflets and commissures from the tubular members.

Figure 5:
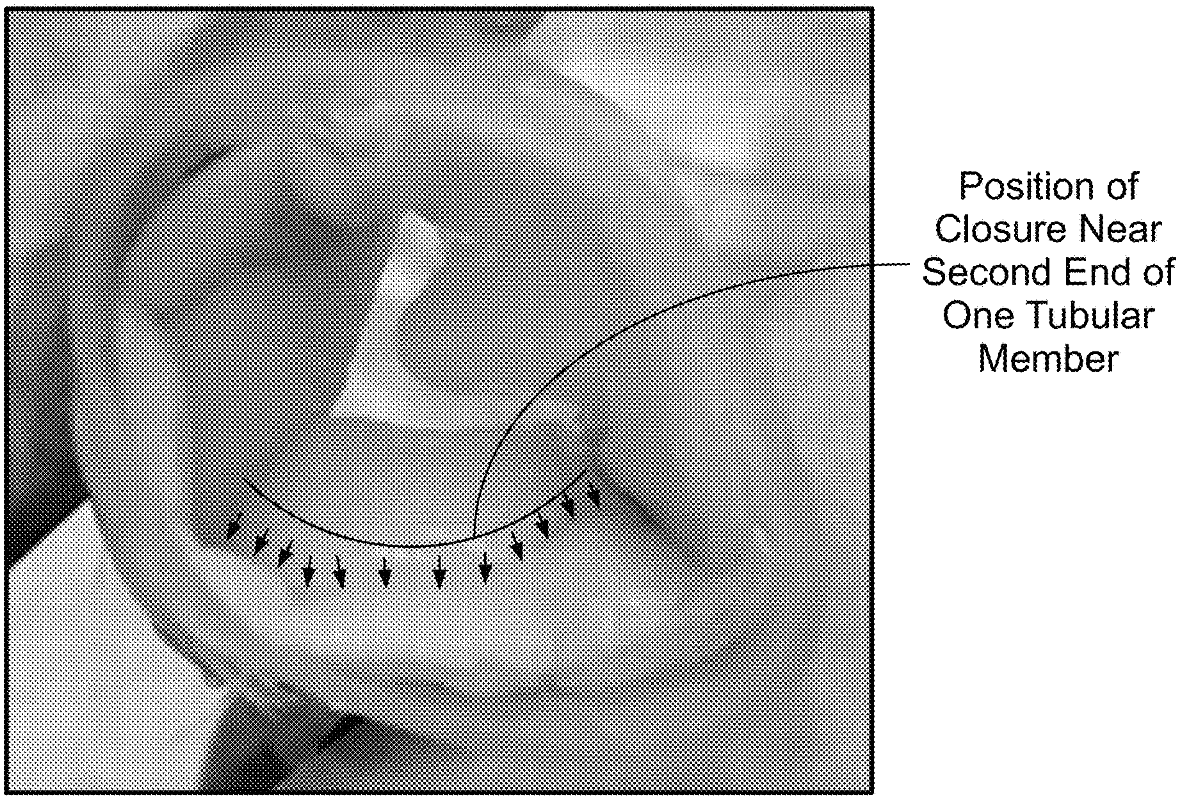
FIG. 5 is a photograph showing an end view (i.e., from the second end) of a prosthetic valve as described herein, specifically showing a seam closing the second end of a tubular member (arrows) within the annulus of a prosthetic valve as described herein.

FIG. 5 is a photograph showing an end view (i.e., a view of the second-end) of a prosthetic valve as described herein and showing the underside of each leaflet (i.e., the closed second ends of each tubular member). The arrows show the seam at the second end of one of the tubular members, which, when closed, produces the leaflet structure.

Figure 6C:
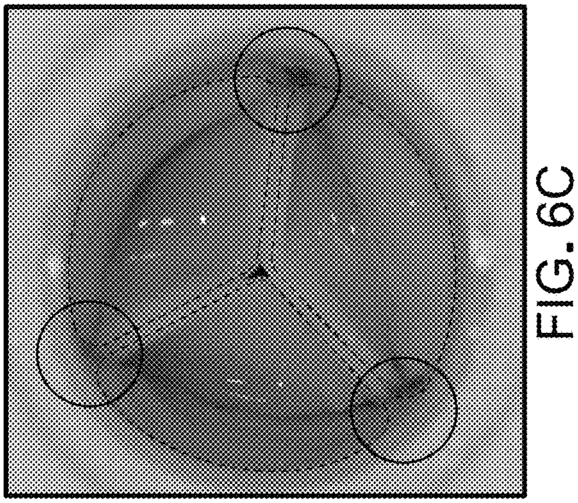
FIG. 6 shows a novel tri-tube valve as described herein. (A) Schematic showing construction of a tri-leaflet valve from three biologically-engineered tubes and degradable suture. (B) Exterior view of the sewn valve. Comparison of the new tri-tube valve (C) and existing tube-in-tube valve (D), with tubes color-coded for clarity and commissures circled to facilitate comparison of how diastolic force on the commissures is born entirely by the connecting sutures for the tube-in-tube valve (C) and predominantly by the tube material for the tri-tube valve (D).
Figure 6D:
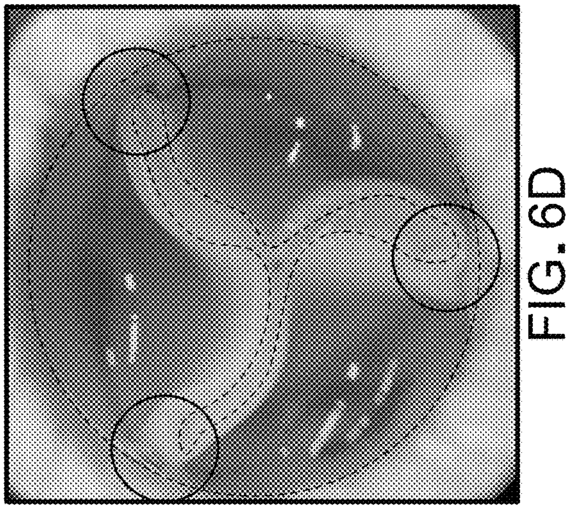
Figure 6B:
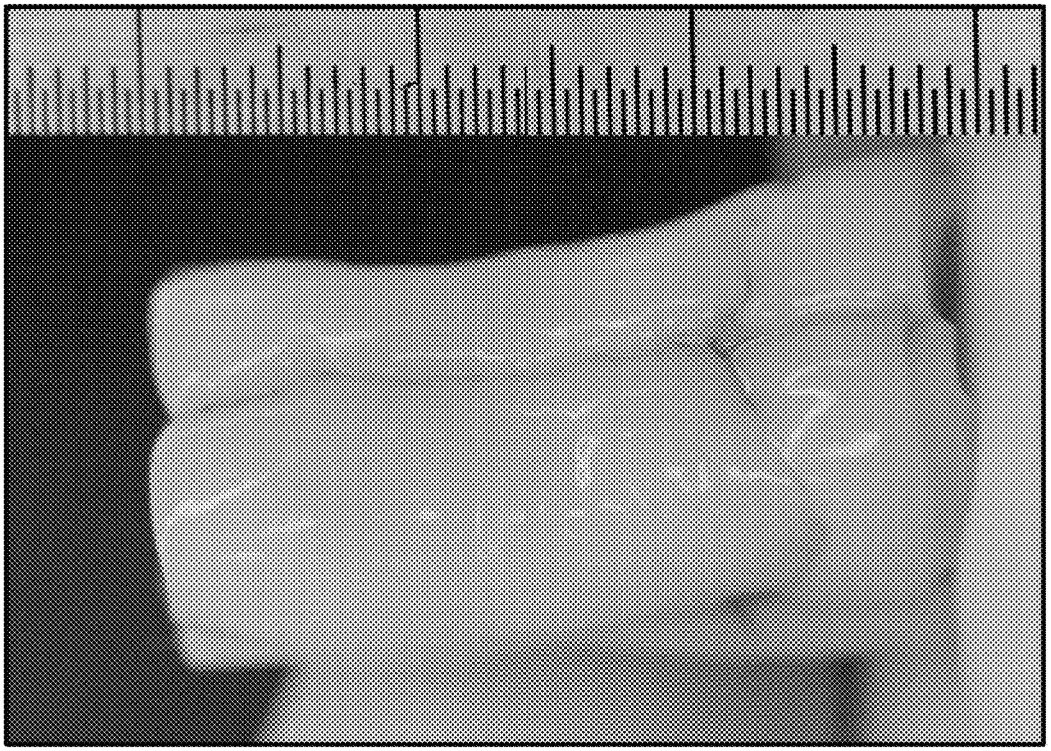
Figure 6A:
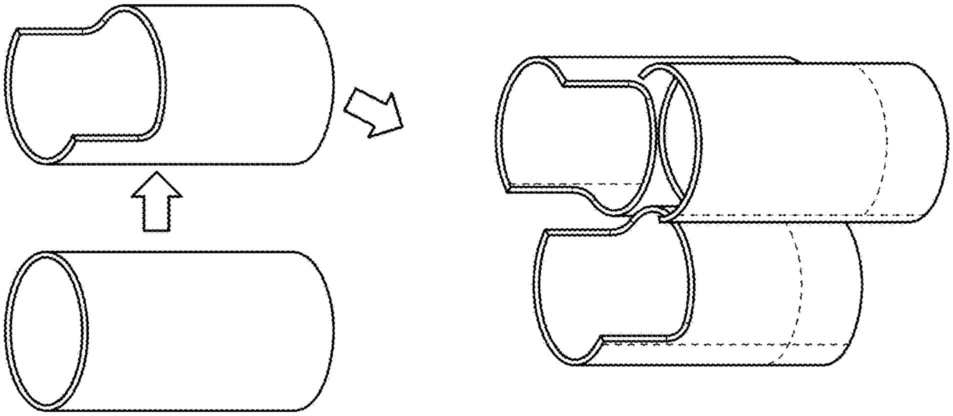
Figure 7A:
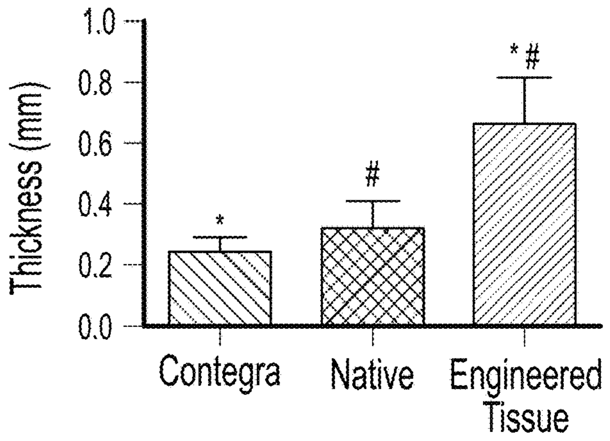
FIG. 7 shows a comparison of tensile mechanical property comparison. Biologically-engineered tube matrix compared to native sheep pulmonary valve leaflet and Contegra™ valve leaflet (A) Thickness, (B) Ultimate Tensile Strength (UTS), and (C) Modulus (n=9). (D) shows a trichrome image of decellularized engineered tube. Scale bar=200 um. Paired symbols indicate significant difference at $p<0.05$.
Figure 7B:
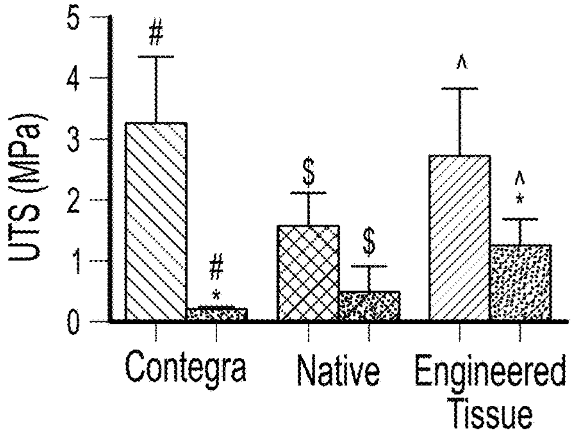
Figure 7C:
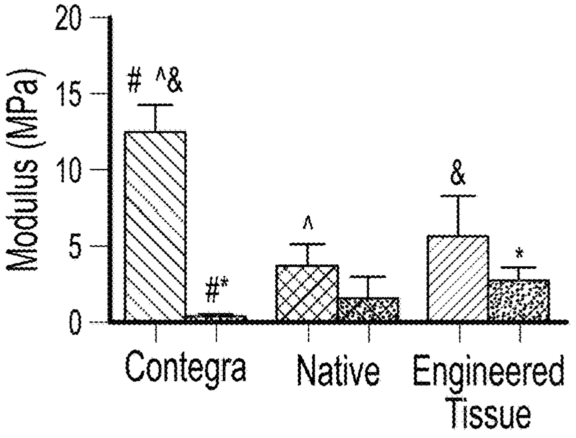
Figure 7D:
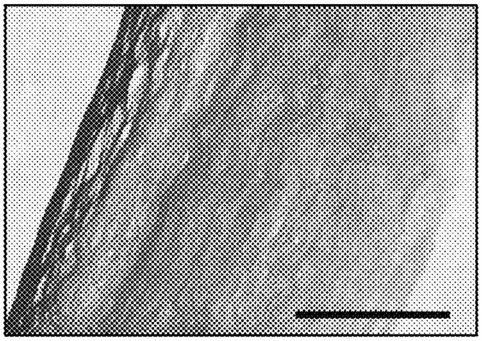

FIGS. 6A-6B shows another embodiment of a tri-tube design in which three tubes are sutured together in a closed ring and then the bottom of each tube is then sutured closed to form its own leaflet (only two of the axial suture lines connecting the three tubes together are clearly seen, along with the complete closure of one of the tubes creating one of the "leaflets").

The design of the prosthetic valve described herein is intended to eliminate the most common site of failure of a valve that is made by suturing one tube inside another, where the load on the leaflets is transferred directly to the sutures used to attach the inner tube to the outer tube at the commissures. In the design described herein, the commissure is created by adjacent tubular members, so the load on the leaflets is carried by the tubular member itself and not the sutures. Thus, "suture pull-out," which is another common problem with many of the currently used prosthetic valves, should not occur with the prosthetic valves described herein.

One of the crucial differences in the commissures with this new tri-leaflet valve design is evident in comparing the connection of the three tubes in the new tri-tube design (see FIG. 1 and FIGS. 6A, 6B and 6D) with the connection of the two tubes in the original tube-in-tube design (see FIG. 6C), where each color represents a tube that was sewn together to form the valves and the circles indicate the commissure locations. It can be gleaned that downward force on the leaflets is going to be predominately carried by the bulk matrix in the new tri-tube design (FIG. 6D) as opposed to the suture in the original tube-in-tube design (FIG. 6C).

Fatigue testing of the novel valve design described herein is presented demonstrating the superior commissure stability of the tri-tube design; pulse duplicator testing is presented showing acceptable valve function under pulmonary valve flow conditions in a juvenile sheep; and valve function upon implantation into the pulmonary artery of a juvenile sheep is show using ultrasonography (following compromise of the native pulmonary valve).

Connecting or joining tissues and the various connectors for doing so are known in the art and include, without limitation, sutures or stitches, staples, adhesives (e.g. cyanoacrylate), or thermal fusion/welding. Such connectors can be used to attach tubular members to adjacent tubular members along a longitudinal seam or to close each tubular member at the second end as described herein.

It also would be understood that, in some embodiments, it may be desirable to include or attach a prosthetic valve as described herein to a solid support or solid structure. See, for example, FIG. 1F. The way in which a prosthetic valve as described herein can be attached to a solid support or a solid structure will be dependent upon the material(s) that each is made from. In some instances, the same type of connectors for connecting or joining tissues that are described herein (e.g., suture/stitches, staples, adhesives (e.g. cyanoacrylate), or thermal fusion/welding) can be used to attach a prosthetic valve to a solid support or solid structure. In some instances, a biologically-engineered prosthetic valve as described herein can be generated on the solid support or solid structure such that the prosthetic valve becomes integral with the solid support or solid structure.

Figure 1G:
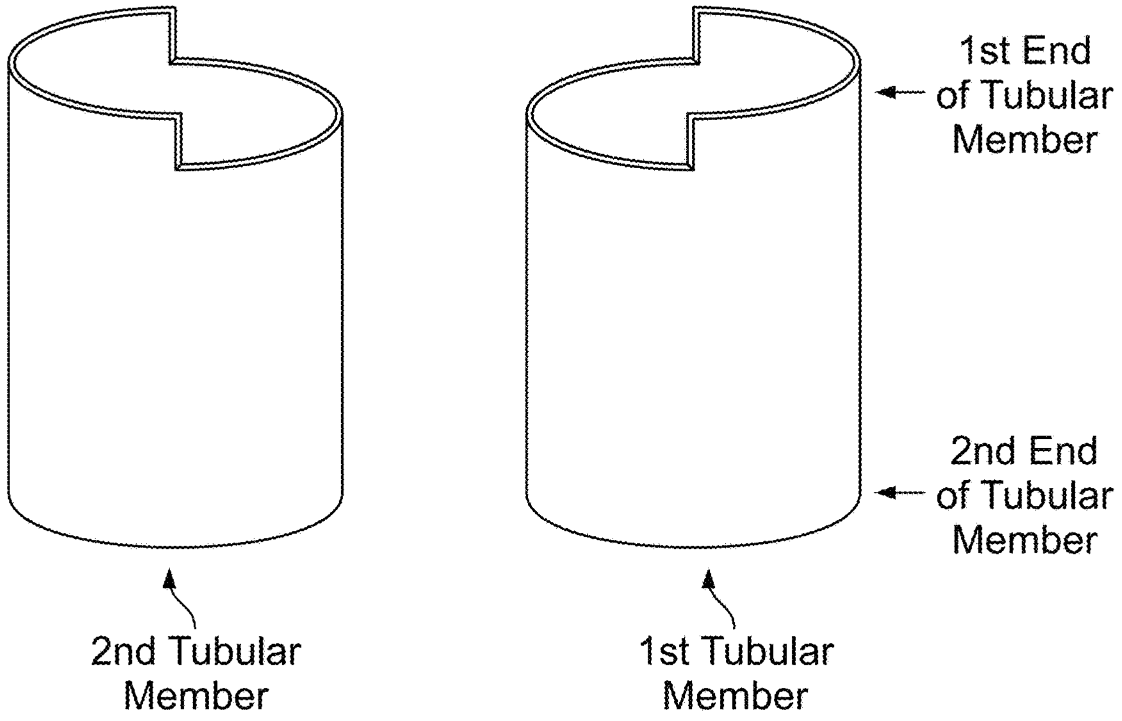
Figure 1H:
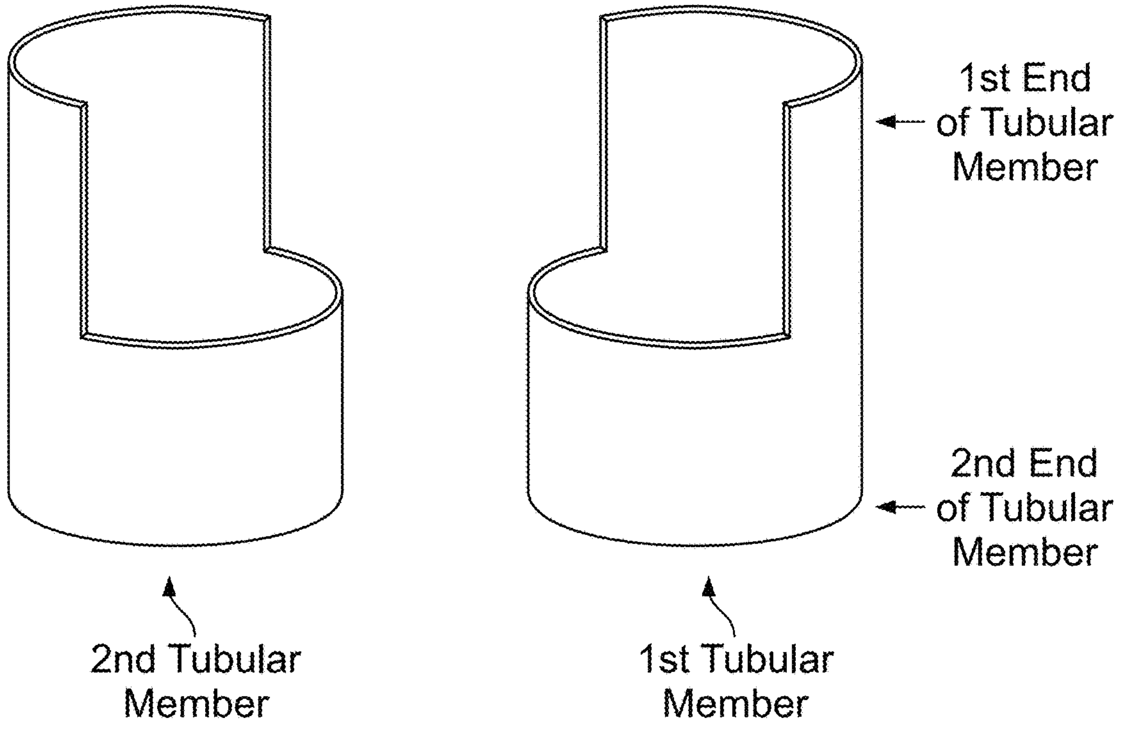

FIGS. 1G and 1H demonstrate that the position of the leaflets within the valve body can be controlled by trimming or eliminating material from the tubular members. Simply by way of example, FIG. 1G shows that a small amount of material can be removed from the portion of the tubular members that is in the interior of the valve body (i.e., that does not form the wall of the valve body), which ultimately results in the leaflets being slightly recessed in the valve body relative to the first end. On the other hand, FIG. 1H shows that a larger amount of material can be removed from the portion of the tubular members that is in the interior of the valve body (i.e., that does not form the wall of the valve body), which ultimately results in the leaflets being positioned deeper in the valve body (e.g., halfway between the first and second ends, or nearer the second end than the first end of the valve body). The position of the leaflets within the valve body as described herein (i.e., relative to the first and second ends of the valve body) will depend upon the type of valve and/or methods of using the prosthetic valve described herein (e.g., strategies for repairing, replacing and/or reconstructing the native valve). It is noted that, while FIGS. 1G and 1H show two tubular members (i.e., a first and a second tubular member), the same concept of trimming or eliminating material to control the position of the valves within the prosthetic valve body can be applied to a prosthetic valve that includes three tubular members or four tubular members.

In addition, one or more non-isodiametric tubular members can be used such that a sinus exists behind the leaflets. Such a sinus can be part of the normal valve anatomy when the diameter of the tube is increased in this region, and is considered important for normal valve hemodynamics.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Tissue Tube Production

Tubular, cell-seeded fibrin gels were fabricated by mixing aqueous solutions of ovine dermal fibroblasts (ODFs, Coriell), bovine fibrinogen (Sigma), thrombin (Sigma), and calcium chloride. The final component concentrations were as follows: 1 million ODFs/mL, 4 mg/mL fibrinogen, 0.38 U/mL thrombin, and 5.0 mM Ca'. The mixed solution was injected into tubular glass molds, which had a 16 mm inner diameter mandrel, a 4 mm annulus, and were 15 cm in total length.

Following gelation, the tubular fibrin gels on glass mandrels were cultured in DMEM+10% fetal bovine serum (FBS, Hyclone), 100 U/mL penicillin, 100 μg/mL streptomycin, 0.25 μg/mL amphotericin B, 2 μg/mL insulin, and 50 μg/mL ascorbic acid. Culture medium was changed three times per week for 2 weeks while allowing the longitudinal shortening of the gels. The tissue tubes were then matured in a pulsed-flow-stretch bioreactor as described (Syedain et al., 2011, Biomaterials, 32(3):714-22).

Following maturation, the biologically-engineered tubes were decellularized by immersion in 1% sodium dodecyl sulfate (SDS, Sigma) and 1% Triton X-100 (Sigma) for 6 hours and 30 minutes, respectively, at room temperature with continuous shaking. The tubes were then extensively rinsed in 1X phosphate buffered saline before and after overnight incubation in culture medium plus 2 U/mL deoxyribonuclease (Worthington Biochemical).

Example 2—Valve Fabrication

Valves of 19 mm in diameter were fabricated using three of the 16 mm diameter biologically-engineered tubes. Each tube was cut to a length of 3 cm and a further trimmed to define a leaflet while providing for an outflow tract (FIG. 6A). The tubes were first sutured together into a closed ring using degradable sutures (Covidien Maxon CV) with three suture lines spanning the length along their point of contact (white dashed lines, FIG. 6A). Then the bottom of each tube was sutured together to create a leaflet (yellow dashed lines, FIG. 6A), yielding a tri-leaflet valve (FIG. 6B). The top view of a tube-in-tube valve and a tri-tube valve with the tubes color coded (FIG. 6C, 6D) facilitates comparison of commissure construction.

Example 3—Accelerator Wear Testing

Valves were mounted on custom silicone fixture and placed in Bose Durapulse™ System. Valves were tested at 20 Hz frequency with end diastolic pressure of 20 mm Hg to mimic pulmonary diastolic pressure gradients. One tube-in-tube valve and one tri-tube valve made from the same batch of biologically-engineered tubes were run for about 12 million (M) cycles prior to visual inspection.

Example 4—Pulse Duplicator Operation

A customized pulse duplicator system as previously described (Reimer et al., 2015, Biomaterials, 62:88-94) was used. It consists of a commercial wave generator and pump (ViVitro Systems), a reservoir, valve mounting chamber, variable compliance chamber, and mechanical bi-leaflet valve to ensure one-directional fluid movement. The system had pressure transducers (ViVitro Systems) immediately above and below the valve to allow for accurate pressure measurements. Additionally, there was an electromagnetic flow meter (Carolina Medical, 500 series flow-meter) upstream of the valve to measure the flow rate in both directions. A custom Labview ° program was used to record flowrates and pressures. For testing, the valve was sewn into two custom silicone sleeves that were then mounted in a custom chamber that allows for applying a transmural pressure gradient (Reimer et al., 2015, Biomaterials, 62:88-94). The pulse duplicator loop was run with phosphate buffered saline as the test fluid. Each valve was tested with pressure conditions to mimic pulmonary pressure conditions at a prescribed flow rate (set by pump stroke volume and frequency). Average flow rate of 3.5 LPM was used to mimic pediatric cardiac output (Cattermole et al., 2017, Physiol. Rep., 5(6):PMCID: 5371563). Pressure was controlled by changing the down-stream flow resistance, stroke volume, and up-stream hydraulic pressure head. During valve testing, end-on camera (Canon EOS T3i) images were obtained at 60 fps for video capture. Images extracted from the video were imported into ImageJ® software to measure the open area of the valve during systole to report the geometric orifice area as percentage of total circular area for a given diameter.

Example 5—Tensile Strain-to-Failure

Strips with dimensions ~2 mm×~10 mm were cut from the biologically-engineered tube in the circumferential and axial directions and tested in tensile strain-to failure as previously described (Syedain et al., 2015, Biomaterials, 73:175-84; Reimer et al., 2015, Biomaterials, 62:88-94). Briefly, sample dimensions were measured prior to testing using a digital caliper. The strips were mounted in custom grips attached to the actuator arms of an Instron tensile testing system (Instron Systems) and straightened with a 0.02 N tensile load. Strain was calculated by taking the natural logarithm of the sample's deformed length over its initial length. Stress was defined as the force divided by the un-deformed, cross-sectional area of the strip. Modulus and ultimate tensile strength (UTS) were taken as the slope of the linear region of the stress-strain curve and the maximum stress recorded, respectively.

Example 6—Suture Pull-Out Force

As previously described (Syedain et al., 2017, Sci. Transl. Med., 9(414): pii: eaan4209), suture pull-out force was measured by placing a loop of 7-0 suture 2 mm from the edge of a strip that is cut 1 cm×1 cm. One end of the loop is clamped to a stationary arm and the other end is connected to the actuator arm of an Instron tensile testing system (Instron Systems). The loop was pulled to failure at a rate of 5 mm/sec.

Example 7—Collagen Content

As previously described (Syedain et al., 2014, Tissue Eng. Part A, 20(11-12):1726-34), leaflet samples approximately 5 mm×5 mm were collected to measure collagen content biochemically. Collagen content is quantified using the hydroxyproline assay and a conversion factor of 7.46 mg of collagen per mg of 4-hydroxyproline. In brief, a graft sample was acid hydrolyzed and dissolved collagen was bound to dimethylaminobenzaldehyde (p-DMBA) as a colorimetric detector. In a 96-well format, hydrolyzed graft samples and hydroxyproline standards were read at 550 nm wavelength in a BioRad plate detection system. Starting sample volumes were calculated using the measured length, width, and thickness of each sample. Collagen contents were reported as collagen mass per unit volume in each sample.

Example 8—Valve Implantation

Implantations were performed at the University of Minnesota Experimental Surgical Services (ESS). The fabricated valves were implanted as pulmonary valve replacements in n=8 Dorset lambs (average age=16±4 weeks, average weight=28±2 kg). All protocols were approved by the Institutional Animal Care and Use Committee (IACUC). All animals were anesthetized using 10 mg/kg Ketamine and 2-6 mg/kg propofol and maintained on 2-4% isoflurane for the duration of the procedure. The heart was exposed via a left lateral thoracotomy with dissection through the intercostal space. Native leaflets were removed, a segment of the pulmonary artery was resected and replaced with the engineered valved conduit and sutured into place using 5-0 running degradable (Maxon™) suture. The distal end was first sutured using a running suture followed by the proximal end. Prior to closing the anastomosis, the valved conduit was allowed to fill with blood to displace air. Once off bypass, epicardial echocardiography was performed with images acquired. Following surgery, animals received subcutaneous injections of 1500 IU heparin BID for the duration of the study. Valve function was measured with transthoracic echocardiography under manual restraint at 1 week following implantation.

Example 9—Statistics

One-way ANOVA with Tukey posthoc test was used to assess differences in tensile mechanical properties at $p<0.05$. Statistical differences in figure plots are indicated with paired symbols.

Example 10—Tissue Tube Properties

As shown in FIG. 7, the decellularized tissue tubes possessed tensile strength comparable to ovine pulmonary valve leaflets and to the standard-of-care for pediatric pulmonary valve replacement, the Contegra™ valved conduit, which is a cross-linked bovine jugular vein valve. The tensile stiffness of the tubes was comparable to the native leaflet and lower than a Contegra leaflet. Tube thickness was 0.66±0.15 mm compared to 0.32±0.09 mm for ovine leaflets (n=3). The tube suture pullout force was 92±13 grams-force (n=9) as compared to 244±31 grams-force (n=3) for native pulmonary artery of a sheep. The collagen concentration was 50±9 mg/ml (n=6) in engineered tissue compared to 44±14 mg/ml (n=3) for native pulmonary artery. Decellularized tissue histology shows collagen bands (stained green) aligned in the circumferential direction with remnant fibrin (stained red) on luminal surface (FIG. 7D).

Example 11—Valve Wear Resistance

Figure 8A:
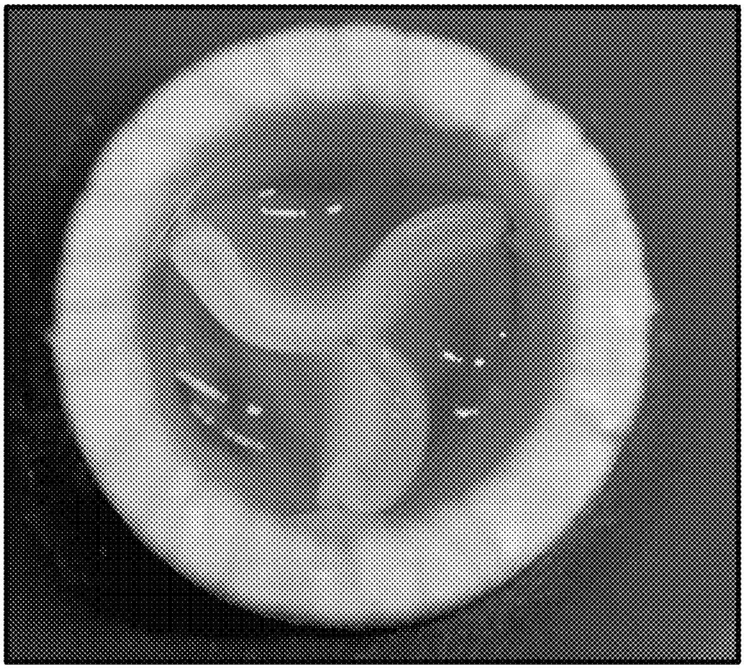
FIG. 8 are photographs showing accelerated wear testing of valve with (A) image of valve mounted in wear tester. Images show damage after 12M cycles to commissures of tube-in-tube valve (B) but not to tri-tube valve (C). Remnant Dacron™ sewing cuff used to facilitate mounting the tri-tube valve in the tester is evident in (C) was located 1.2 mm above the commissure, hence, providing negligible structural support to the commissure.
Figure 8B:
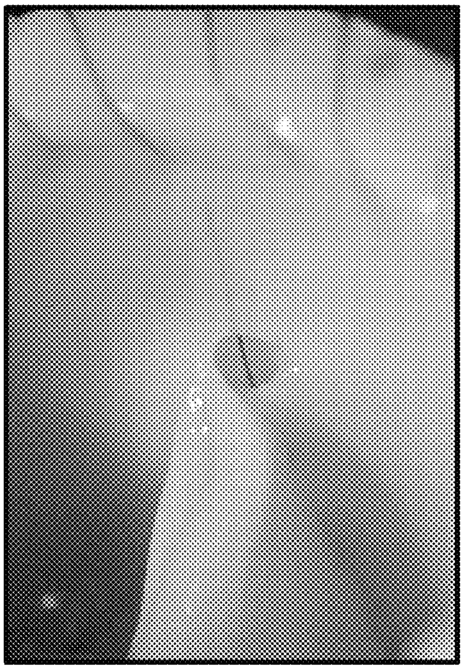
Figure 8C:

Wear resistance was assessed in accelerated fatigue testing using a Bose Durapulse™ System after 12 M cycles (equivalent to 20 wk in vivo) with 20 mm Hg end diastolic pressure drop (FIG. 8A). Commissure damage was clearly evident in the tube-in-tube design at the suture sites connecting the inner and outer tubes at the commissures (FIG. 8A), but not in the novel tri-tube design (FIG. 8B) where the commissures are formed by adjoining tubes (FIG. 6A-6C).

Example 12—Valve Hydrodynamics

Figure 9A:
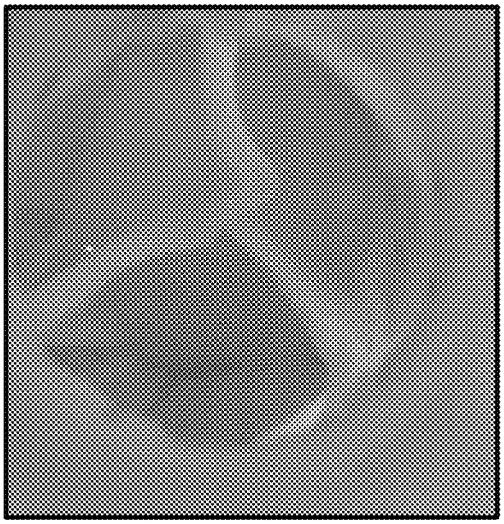
FIG. 9 shows a pulse duplicator system for valve performance measurements. End on view of valve mounted in (A) closed and (B) open position. (C) Pressure and flow-rate traces for 3 cycles of valve under pulmonary valve flow conditions. During diastolic phase, the process of fluid moving from reservoir through a mechanical valve into pump leads to pressure pulse that cause equalization of pressure across the valve leading to positive flow as can be seen in flow profile.
Figure 9B:
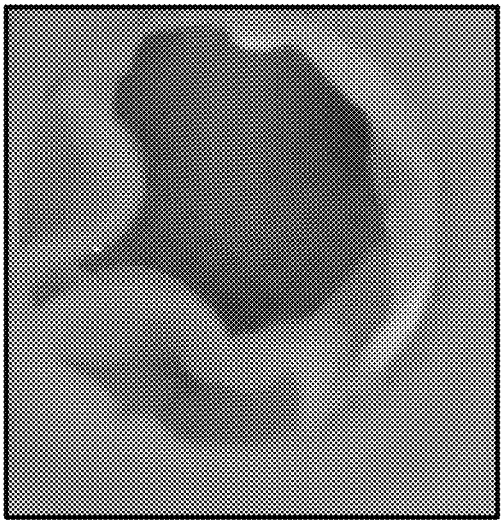
Figure 9C:
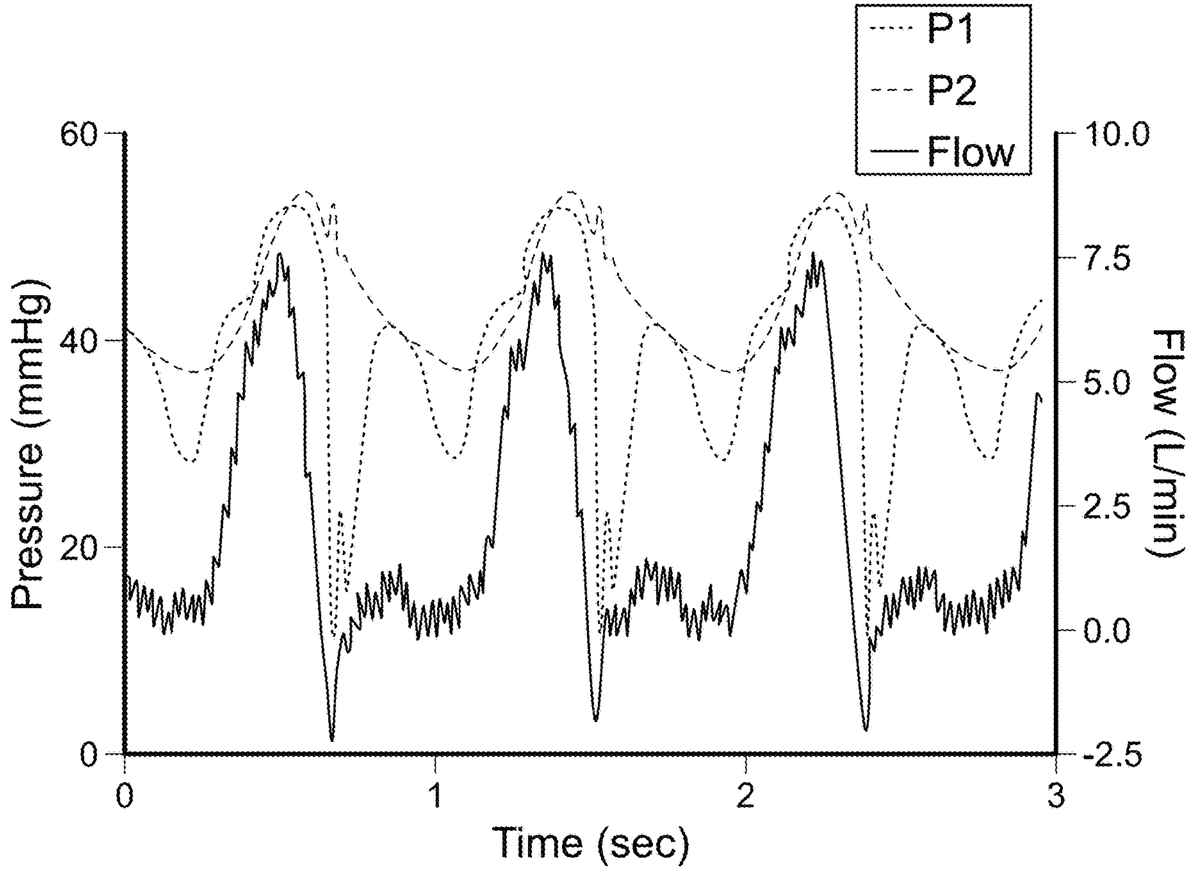

As would be expected based on the close agreement of tensile properties between the biologically-engineered tubes and valve leaflets (FIG. 7), the hemodynamic performance of a valve constructed from these tubes of cell-produced collagenous matrix (FIG. 9) is acceptable, with <2 mm Hg systolic pressure gradient and <15% closing volume/regurgitation, as shown in the comparison of pulse duplicator testing data of the Contegra™ valve.

TABLE 1

Pulse Duplicator Testing Summary of Tri-tube Valve Compared with Contegra ™

| Parameter | Contegra ™ 16 mm (n = 1) | Tri-tube Valve 19 mm (n = 2) |
|---|---|---|
| Mean Systolic ΔP (mm Hg) | 3.3 | 1.3-2.1 |
| Mean Flow Rate (LPM) | 3.4 | 3.9 |
| Closing Volume Fraction | 7.3% | 1.8-12.6% |
| Geometric Orifice Area | 52% | 59-65% |

Example 13—Valve Function at Implantation

Figure 10A:
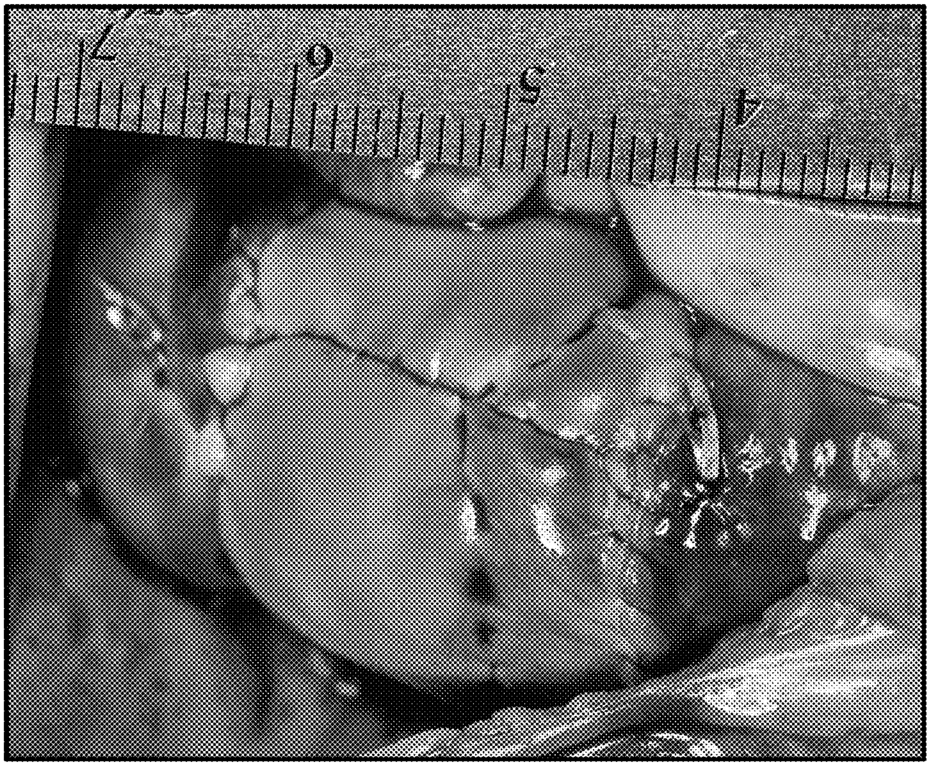
FIG. 10 are photographs showing implantation of 19 mm tri-tube valve into a juvenile sheep. Surgical field (A), and epicardial echocardiographic images during diastole in long (B) and short (C) axis views. Arrows indicate "leaflets." Color doppler during valve in (D) systole, showing a large valve orifice, and (E) diastole, showing no regurgitation.
Figure 10B:
Figure 10C:
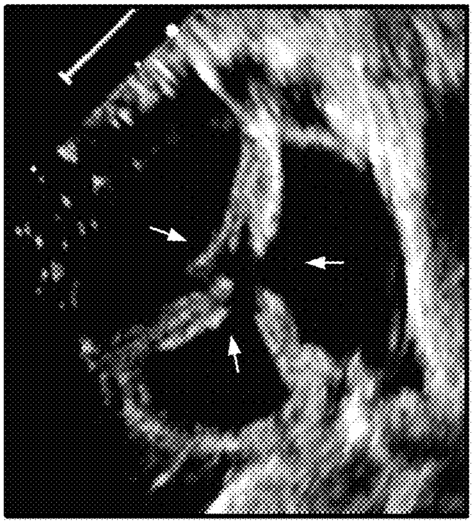
Figure 10D:
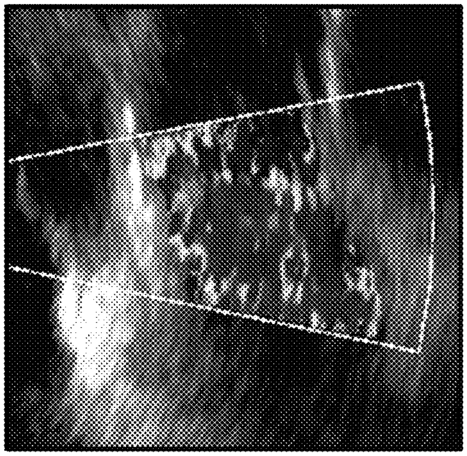
Figure 10E:
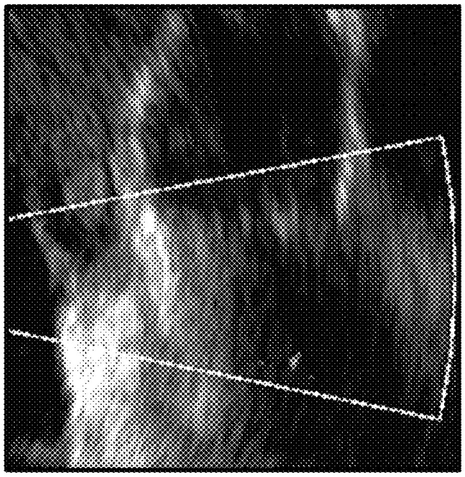

Four juvenile sheep (average 4 mo old, 28 kg) were implanted interpositionally with a tri-tube valve in the pulmonary artery after removing the leaflets of the native pulmonary valve, and 3D epicardial echocardiography was performed at implantation. Representative surgical field and ultrasound images for the tri-tube valve immediately post-implantation are shown in FIG. 10. The measured coaptation length of the leaflets taken from the long axis view was 3-5 mm (FIG. 10B). Valve performance metrics from the ultrasound analysis conducted 1-week post-op are reported. All valve leaflets had normal leaflet motion with full coaptation during diastole and nil regurgitation. Systolic pressure drop across the valves was <5 mm Hg except in one animal where a narrow distal anastomosis, as sutured, created a systolic pressure drop of 15 mm Hg.

TABLE 2

Ultrasound Assessment of Implanted Tri-tube Valve at 1 Week Post-Implantation

| Animal ID | Cardiac Output (LPM) | Mean Systolic ΔP (mm Hg) | Effective Orifice Area ($cm^2$) | Pulmonary Insufficiency Index |
|---|---|---|---|---|
| PACV 1 | 4.1 | 15[a] | 0.88 | Trivial |
| PACV 2 | 7.2 | 5 | 1.37 | Trivial |
| PACV 3 | 4.2 | 2 | 0.92 | Trivial |
| PACV 4 | 4.9 | 3 | 0.94 | Trivial |

[a]Systolic pressure was high due to cinching at distal anastomotic suture line

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A decellularized, tri-tube valve, comprising:
a body comprising a first end, a second end, an outer surface, and an annular region, and defining a longitudinal axis, the body comprising three tubular members aligned with the longitudinal axis;
wherein each tubular member is fixedly attached to an adjacent tubular member along an adjoining exterior surface in a direction along the longitudinal axis such that portions of the exterior surface of the adjoined tubular members circumferentially form a wall of the body;
wherein each tubular member is fixedly closed at the second end, a luminal surface of each tubular member defining a top surface of a leaflet, wherein the portions of the exterior surface at the first end of the adjoined tubular members that do not form the wall of the body define commissures, wherein each leaflet comprising a commissure region and a contiguous annulus region are formed by each tubular member.

2. The decellularized, tri-tube valve of claim 1, wherein each commissure is created by adjacent tubular members.

3. The decellularized, tri-tube valve of claim 1, wherein the valve is selected from the group consisting of a mitral valve, an aortic valve, tricuspid valves, pulmonary heart valves, and vein valves.

4. A decellularized, tri-tube valve, comprising a body comprising three adjoined tubular members sealed at one end, wherein each sealed tubular member forms a leaflet, wherein each leaflet comprises a commissure region that is contiguous with an annulus region.

5. The decellularized, tri-tube valve of claim 4, wherein each commissure is created by adjacent tubular members.

6. The decellularized, tri-tube valve of claim 4, wherein the valve is selected from the group consisting of a mitral valve, an aortic valve, tricuspid valves, pulmonary heart valves, and vein valves.

7. A decellularized, tri-tube valve, comprising:
a body defining a longitudinal axis; the body comprising three leaflets, each leaflet being defined by a tubular member aligned with the longitudinal axis,
three tubular members, each tubular member comprising a first end, a second end, an exterior surface, and a luminal surface; the first end of each tubular member being open and the second end of each tubular member being closed such that the luminal surface of the tubular member forms a top surface of a leaflet, wherein each leaflet comprises a commissure region that is contiguous with an annulus region.

8. The decellularized, tri-tube valve of claim 7, wherein each commissure is created by adjacent tubular members.

9. The decellularized, tri-tube valve of claim 7, wherein the valve is selected from the group consisting of a mitral valve, an aortic valve, tricuspid valves, pulmonary heart valves, and vein valves.

10. A method of making a decellularized, tri-tube valve, comprising:
providing three tubular members, each of the tubular members comprising a tubular member first end, a tubular member second end, an exterior surface, and a luminal surface and defining a tubular member longitudinal axis;

aligning the three tubular members along the tubular member longitudinal axis;

attaching adjacent tubular members along an adjoining exterior surface in a direction along the tubular member longitudinal axis to form a body, the body comprising a body first end, a body second end, an outer surface, and annular region, and defining a body longitudinal axis, wherein portions of the exterior surface of the adjoined tubular members circumferentially form a wall of the body; and closing each tubular member at the tubular member second end such that the luminal surface of each tubular member defines a top surface of a leaflet, wherein the portions of the exterior surface at the first end of the adjoined tubular members that do not form the wall of the body define commissures, wherein each leaflet comprising a commissure region and a contiguous annulus region are formed by each tubular member.

11. The method of claim 10, wherein each commissure is created by adjacent tubular members.

12. The method of claim 10, wherein at least one of the tubular members is a native tissue tubular member, a biologically-engineered tubular member, or a synthetic tubular member.

13. The method of claim 12, wherein the biologically-engineered tubular member is generated from fibrinogen, thrombin, and extracellular matrix-producing cells.

14. The method of claim 10, wherein the body comprises at least one native tissue tubular member, at least one biologically-engineered tubular member, or at least one synthetic tubular member.

15. The method of claim 14, wherein the biologically-engineered tubular member is generated from fibrinogen, thrombin, and extracellular matrix-producing cells.

16. The method of claim 10, wherein the attaching is with stitches, staples, adhesives, or thermal fusion/welding.

17. The method of claim 10, wherein the closing is with stitches, staples, adhesives, or thermal fusion/welding.

* * * * *